(12) United States Patent
Fukizawa et al.

(10) Patent No.: US 11,066,629 B2
(45) Date of Patent: Jul. 20, 2021

(54) LIPID METABOLISM-PROMOTING COMPOSITION INCLUDING ISOXANTHOHUMOL

(71) Applicant: SUNTORY HOLDINGS LIMITED, Osaka (JP)

(72) Inventors: Shinya Fukizawa, Kyoto (JP); Mai Yamashita, Kyoto (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 0 days.

(21) Appl. No.: 16/471,851

(22) PCT Filed: Dec. 18, 2017

(86) PCT No.: PCT/JP2017/045364
§ 371 (c)(1),
(2) Date: Jun. 20, 2019

(87) PCT Pub. No.: WO2018/117041
PCT Pub. Date: Jun. 28, 2018

(65) Prior Publication Data
US 2019/0381001 A1 Dec. 19, 2019

(30) Foreign Application Priority Data
Dec. 20, 2016 (JP) .............................. JP2016-246974

(51) Int. Cl.
| A61K 31/353 | (2006.01) |
| C12G 3/055 | (2019.01) |
| A61P 3/04 | (2006.01) |
| A61K 9/00 | (2006.01) |
| A61K 47/40 | (2006.01) |
| A61K 47/46 | (2006.01) |

(52) U.S. Cl.
CPC ............ *C12G 3/055* (2019.02); *A61K 9/0095* (2013.01); *A61K 31/353* (2013.01); *A61K 47/40* (2013.01); *A61K 47/46* (2013.01); *A61P 3/04* (2018.01)

(58) Field of Classification Search
CPC ..................................................... A61K 31/12
See application file for complete search history.

(56) References Cited

U.S. PATENT DOCUMENTS

| 2006/0233902 | A1  | 10/2006 | Yajima et al. |
| 2007/0218155 | A1  | 9/2007  | Kuhrts |
| 2009/0209654 | A1* | 8/2009  | Kuhrts ...................... A61P 9/00 514/685 |
| 2010/0029757 | A1* | 2/2010  | Hellerbrand .............. A61P 1/16 514/456 |
| 2016/0008298 | A1  | 1/2016  | Stevens |

FOREIGN PATENT DOCUMENTS

| JP | 2006-306800 | 11/2006 |
| JP | 2007-289185 | 11/2007 |
| WO | 03/068205   | 8/2003  |

OTHER PUBLICATIONS

Yang et al. CAS: 148: 206423, 2007.*
Miranda et al., "Xanthohumol improves dysfunctional glucose and lipid metabolism in diet-induced obese C57BL/6J mice", *Arch. Biochem. Biophys.*, vol. 599, pp. 22-30 (2016).
Yang et al., "Effect of xanthohumol and isoxanthohumol on 3T3-L1 cell apoptosis and adipogenosis", *Apoptosis*, vol. 12, No. 11, pp. 1953-1963 (2007).
Hosoya, "Screening of polyphenols targeting for apoptosis inhibitor of macrophage (AIM) on anti-obesity", *Shokuseitatsu kagaku, bunko oyobi kankyou ni kansuru kenkyuu josei kenkyuu kiyou*, 28, 21-28 (2013), including English-language Abstract.
Yang et al., "Conformational modulation of the farnesoid X receptor by prenylflavonoids: Insights from hydrogen deuterium exchange mass spectrometry (HDX-MS), flourescence titration and molecular docking studies", *Biochimica et Biophysica Acta*, vol. 1864, pp. 1667-1677 (2016).
International Search Report issued in PCT/JP2017/045364, dated Mar. 20, 2018, along with an English-language translation.
Kiyofuji et al., "Effects of Xanthohumol-Rich Hop Extract on the Differentiation of Preadipocytes," *J. Oleo Sci.*, vol. 63, No. 6, pp. 593-597 (2014).

\* cited by examiner

*Primary Examiner* — Rei Tsang Shiao
(74) *Attorney, Agent, or Firm* — Greenblum & Bernstein, P.L.C.

(57) ABSTRACT

The present invention aims to provide a composition for promoting lipid metabolism, a composition for suppressing fat accumulation, and the like, which contain, as an active ingredient, a substance that is thermally stable and adequately water-soluble and that has lipid metabolism-promoting action. The present invention relates to a composition for promoting lipid metabolism containing isoxanthohumol.

3 Claims, 5 Drawing Sheets

LIPID METABOLISM-PROMOTING COMPOSITION INCLUDING ISOXANTHOHUMOL

TECHNICAL FIELD

The present invention relates to a composition for promoting lipid metabolism and a composition for suppressing fat accumulation. The present invention also relates to a composition for anti-obesity. The present invention also relates to a method of promoting lipid metabolism, a method of suppressing fat accumulation, and a method of preventing or ameliorating obesity. The present invention further relates to use of isoxanthohumol in promoting lipid metabolism, suppressing fat accumulation, or preventing or ameliorating obesity.

BACKGROUND ART

Due to factors such as high calorie diet and lack of exercise, excessive fat accumulates systemically or locally, causing obesity. Obesity is a cause of various lifestyle-related diseases, and is also a social problem. Thus, intensive studies have been made to search for an ingredient effective in obesity prevention or amelioration and applicable to pharmaceutical products, foods for specified health uses, functional foods, and the like.

Xanthohumol is known as a component of hops (scientific name: *Humulus lupulus*) that are a plant of the family Cannabaceae and are used as raw materials of beer. Xanthohumol is a polyphenol having a molecular formula represented by $C_{21}H_{22}O_5$, and is particularly classified as "prenylchalcone" within polyphenols. Xanthohumol has been reported to have the following physiological activities: carcinogenesis inhibitory action, anti-inflammatory action, anti-obesity action, and bone resorption inhibitory action, for example.

Non-Patent Literature 1 describes, for example, suppression of body weight increase in a high-fat diet mouse model by a repeated dose of xanthohumol in an amount of 30 mg/kg/day. Patent Literature 1 describes a tendency of suppression of body weight gain and a decrease in the weight of fat around kidney or the like in a type II diabetes mouse model fed with feed containing xanthohumol at a concentration of 1%.

Xanthohumol is irreversibly structurally converted into isoxanthohumol when heated. In particular, it has been reported that a large portion of xanthohumol is converted into isoxanthohumol during beer brewing.

Non-Patent Literature 2 reports enhanced expression of lipolysis-promoting factor "apoptosis inhibitor of macrophage" (AIM) in mouse macrophage-derived cells (J774.1) cultured with addition of isoxanthohumol. Yet, Non-Patent Literature 2 states that whether or not isoxanthohumol actually reduces lipid droplets is unknown because isoxanthohumol treatment at a concentration without cytotoxicity to mouse preadipocyte (3T3-L1) did not suppress differentiation of the cells into adipocytes, failing to confirm the effect of isoxanthohumol as a phenotype that reduces lipid droplets.

According to a report, while xanthohumol and isoxanthohumol both have prenyl groups, the former has a chalcone skeleton as a partial structure and the latter has a flavanone skeleton as a partial structure, with different physicochemical properties and physiological activities therebetween. Patent Literature 2 states that while xanthohumol has very effective anticancer action, isoxanthohumol hardly has anticancer action. Thus, it is difficult to analogize the physiological activity of isoxanthohumol based on information regarding the physiological activity of xanthohumol.

CITATION LIST

Patent Literatures

Patent Literature 1: JP 2006-306800 A
Patent Literature 2: JP 2007-289185 A

Non-Patent Literatures

Non-Patent Literature 1: Arch Biochem Biophys. 2016 Jun. 1; 599: 22-30.
Non-Patent Literature 2: Takahiro HOSOYA, "Screening of polyphenols targeting for apoptosis inhibitor of macrophage (AIM) on anti-obesity", Study help study bulletin about science of eating habits, culture and the environment (*Shokuseikatsu kagaku, bunka oyobi kankyou ni kansuru kenkyuu josei kenkyuu kiyou*) 28, 21-28, 2013, Asahi Group Foundation

SUMMARY OF INVENTION

Technical Problem

According to Patent Literature 1 and Non-Patent Literature 1, xanthohumol showed body weight increase-suppressing action and the like at the animal experiment level. Yet, no such anti-obesity action has been reported regarding isoxanthohumol produced by irreversible structural conversion of xanthohumol when heated. According to Non-Patent Literature 2, isoxanthohumol has enhanced expression of lipolysis-promoting factor AIM in mouse macrophage-derived cells, but the literature states that whether or not isoxanthohumol actually reduces lipid droplets is unknown.

In addition, in the beverage production, for example, products need to be heated under sterilization conditions based on the Food Sanitation Act, and ingredients of beverages need to be water-soluble. It is thus difficult to produce beverages containing more than a certain amount of xanthohumol that is thermally unstable and hardly water-soluble. Thus, a substance that is thermally stable and adequately water-soluble and that contributes to obesity prevention or amelioration has been required.

The present invention aims to provide a composition for promoting lipid metabolism, a composition for suppressing fat accumulation, and the like, which contain, as an active ingredient, a substance that is thermally stable and adequately water-soluble and that has lipid metabolism-promoting action.

Solution to Problem

As a result of intensive studies to solve the above problems, the present inventors discovered that isoxanthohumol shows fat accumulation-suppressing action. Isoxanthohumol showed better fat accumulation-suppressing action than catechins that are used as functional food materials. The present inventors also studied expression of genes related to lipid metabolism in the liver and brown adipose tissue, for example, and found that isoxanthohumol promotes fat burning and has lipid metabolism-promoting action. Examples of approaches leading to promotion of lipid metabolism include a method of suppressing fat synthesis, a method of promoting decomposition of accumulated fat (lipolysis), and a method of promoting fat burning (fat consumption) that converts fatty acids into energy. For example, lipolysis refers to a reaction process that involves hydrolysis of triglyceride into glycerol and free fatty acids. The reaction proceeds by action of lipases in adipose tissue. Fat burning refers to a process that involves conversion of fatty acids produced by lipolysis or the like into energy in the form of heat or ATP, for example. It can be regarded as a reaction that proceeds by action of various enzymes localized in mitochondria and peroxisomes which are intracellular organelles. Thus, the mechanism of action is different, for example, between promotion of decomposition of accumulated fat and promotion of fat burning. It was a surprising finding that isoxanthohumol has action that promotes fat burning to promote lipid metabolism and thus provides a fat accumulation-suppressing effect and an anti-obesity effect. The present inventors also confirmed that isoxanthohumol has higher water-solubility than xanthohumol and found applicability of isoxanthohumol to various beverages and the like because isoxanthohumol is highly suitable for beverage applications as compared to xanthohumol. The present invention was thus completed.

Isoxanthohumol is a substance that is also found in a trace amount in hops (*Humulus lupulus*), and it shows lipid metabolism-promoting action and is highly suitable for beverage applications. Thus, with use of isoxanthohumol, it is possible to develop functional beverages and the like which are highly safe and contribute to maintenance and improvement of health.

Specifically, the present invention relates to the following composition for promoting lipid metabolism, composition for suppressing fat accumulation, and the like.

The composition for promoting lipid metabolism of the present invention contains isoxanthohumol.

In an embodiment, the composition for promoting lipid metabolism of the present invention is preferably a composition for promoting lipid metabolism which promotes lipid metabolism by promoting fat burning.

In an embodiment, the present invention provides a composition for promoting lipid metabolism which promotes lipid metabolism by promoting fatty acid β-oxidation or thermogenesis. In an embodiment, the present invention provides a composition for promoting lipid metabolism which promotes lipid metabolism by activating mitochondrial function.

The composition for promoting lipid metabolism of the present invention is preferably a food or beverage.

In an embodiment, the composition for promoting lipid metabolism of the present invention is preferably a beverage, wherein the beverage is preferably a tea-based beverage, coffee beverage, alcohol beverage, non-alcoholic beer, carbonated beverage, functional beverage, fruit and/or vegetable-based beverage, lactic beverage, soy milk beverage, or flavored water.

The composition for promoting lipid metabolism of the present invention may be one labeled with one or more of the following function claims: "anti-obesity", "obesity prevention", "obesity amelioration", "waist circumference reduction", "waist circumference maintenance", "slim body maintenance", "suppression of body fat accumulation", "body fat reduction", "suppression of visceral fat accumulation", "visceral fat reduction", "suppression of fat accumulation in the liver", "fat reduction in the liver", "weight loss", "weight reduction", "diet", "fat burning", "fat consumption", "lipid metabolism", "mitochondrial function", "thermogenesis", "basal metabolism", "metabolic function", "metabolic capacity", "metabolic syndrome prevention", and "metabolic syndrome amelioration".

The composition for suppressing fat accumulation of the present invention contains isoxanthohumol.

In an embodiment, the composition for suppressing fat accumulation of the present invention is preferably used to suppress visceral fat accumulation or fat accumulation in the liver.

In an embodiment, the present invention provides a composition for suppressing fat accumulation for suppressing fat accumulation by promoting fat burning.

The composition for suppressing fat accumulation of the present invention is preferably a food or beverage.

In an embodiment, the composition for suppressing fat accumulation of the present invention is preferably a beverage. When the composition for suppressing fat accumulation of the present invention is a beverage, the beverage is preferably a tea-based beverage, coffee beverage, alcohol beverage, non-alcoholic beer, carbonated beverage, functional beverage, fruit and/or vegetable-based beverage, lactic beverage, soy milk beverage, or flavored water.

The composition for suppressing fat accumulation of the present invention may be one labeled with one or more of the following function claims: "anti-obesity", "obesity prevention", "obesity amelioration", "waist circumference reduction", "waist circumference maintenance", "slim body maintenance", "suppression of body fat accumulation", "body fat reduction", "suppression of visceral fat accumulation", "visceral fat reduction", "suppression of fat accumulation in the liver", "fat reduction in the liver", "weight loss", "weight reduction", "diet", "fat burning", "fat consumption", "lipid metabolism", "mitochondrial function", "thermogenesis", "basal metabolism", "metabolic function", "metabolic capacity", "metabolic syndrome prevention", and "metabolic syndrome amelioration".

The composition for suppressing fat accumulation of the present invention may be one labeled with one or more of the following function claims: "suppression of body fat accumulation", "body fat reduction", "suppression of visceral fat accumulation", "visceral fat reduction", "metabolic syndrome prevention", and "metabolic syndrome amelioration".

The composition for anti-obesity of the present invention is a composition for anti-obesity containing isoxanthohumol, which is for preventing or ameliorating obesity by promoting lipid metabolism.

In an embodiment, the composition for anti-obesity is preferably a composition for anti-obesity which promotes lipid metabolism by promoting fat burning.

The composition for anti-obesity of the present invention is preferably a food or beverage.

In an embodiment, the composition for anti-obesity of the present invention is preferably a beverage. When the composition for anti-obesity of the present invention is a beverage, the beverage is preferably a tea-based beverage, coffee beverage, alcohol beverage, non-alcoholic beer, carbonated beverage, functional beverage, fruit and/or vegetable-based beverage, lactic beverage, soy milk beverage, or flavored water.

The composition for anti-obesity of the present invention may be one labeled with one or more of the following function claims: "anti-obesity", "obesity prevention", "obesity amelioration", "waist circumference reduction", "waist circumference maintenance", "slim body maintenance", "suppression of body fat accumulation", "body fat reduction", "suppression of visceral fat accumulation", "visceral fat reduction", "suppression of fat accumulation in the liver", "fat reduction in the liver", "weight loss", "weight reduction", "diet", "fat burning", "fat consumption", "lipid metabolism", "mitochondrial function", "thermogenesis", "basal metabolism", "metabolic function", "metabolic capacity", "metabolic syndrome prevention", and "metabolic syndrome amelioration".

The present invention also encompasses the following methods and uses:

a method of promoting lipid metabolism, including administering isoxanthohumol;

a method of suppressing fat accumulation, including administering isoxanthohumol;

a method of preventing or ameliorating obesity, including administering isoxanthohumol to promote lipid metabolism;

use of isoxanthohumol in promoting lipid metabolism;

use of isoxanthohumol in suppressing fat accumulation; and use of isoxanthohumol in preventing or ameliorating obesity by promoting lipid metabolism.

Advantageous Effects of Invention

The present invention can provide a composition for promoting lipid metabolism, a composition for suppressing fat accumulation, and the like, which contain, as an active ingredient, a substance that is thermally stable and adequately water-soluble and that has lipid metabolism-promoting action.

DESCRIPTION OF EMBODIMENTS

The composition for promoting lipid metabolism, the composition for suppressing fat accumulation, and the composition for anti-obesity of the present invention contain isoxanthohumol.

Isoxanthohumol shows lipid metabolism-promoting action. Isoxanthohumol also shows fat accumulation-suppressing action and anti-obesity action that prevents or ameliorates obesity. Isoxanthohumol also shows body weight increase (body weight gain)-suppressing action. Thus, isoxanthohumol is suitably used as an active ingredient of the composition for promoting lipid metabolism, the composition for suppressing fat accumulation, and the composition for anti-obesity. The composition for promoting lipid metabolism, the composition for suppressing fat accumulation, and the composition for anti-obesity of the present invention each contain isoxanthohumol as an active ingredient, and thereby achieve a lipid metabolism-promoting effect, a fat accumulation-suppressing effect, and an obesity-preventing or ameliorating effect. Hereinafter, the composition for promoting lipid metabolism, the composition for suppressing fat accumulation, and the composition for anti-obesity of the present invention are collectively referred to as "the composition for promoting lipid metabolism or the like of the present invention". In an embodiment, the composition for promoting lipid metabolism or the like of the present invention can also be used as a composition for suppressing body weight increase.

Isoxanthohumol can be prepared, for example, through a process such as heating of a hop (*Humulus lupulus*) extract. Heating a hop extract can produce isoxanthohumol in the extract. A hop extract is usually prepared through a process involving extraction of hop cones with a solvent and purification as needed. A hop extract can be obtained by a known preparation method. Hops can be extracted, for example, by a method that uses an ethanol solvent, which is used as a preparation method of a hop extract for beer brewing. A hop extract is commercially available, and a commercial hop extract can also be used. Heating of a hop extract to produce isoxanthohumol is preferably performed at 80° C. to 140° C. (more preferably 85° C. to 100° C.) for 15 minutes to 5 hours (more preferably 20 minutes to 3 hours). Purification of a hop extract to prepare isoxanthohumol is performed by a known method. Purification is performed by, for example, a method using HPLC or an absorption column or a precipitation method based on changes in solubility. Isoxanthohumol can also be produced by heating xanthohumol. Here, the heating temperature is preferably 80° C. to 140° C. (more preferably 85° C. to 100° C.) for 15 minutes to 5 hours (more preferably 20 minutes to 3 hours).

It has been reported that isoxanthohumol is stable even at a high temperature of 100° C., for example. The Food Sanitation Act defines sterilization conditions as the production standard of soft drinks. For example, soft drinks having a pH of 4.0 or higher need to be heated at 85° C. for 30 minutes. In view of ingredient conversion in such sterilization, isoxanthohumol is considered to be highly suitable for beverage applications as compared to xanthohumol which is thermally unstable. Isoxanthohumol is also highly water-soluble as compared to xanthohumol, and thus advantageously can be easily used in beverages, for example. Thus, the present invention can provide various functional beverages that show lipid metabolism-promoting action, fat accumulation-suppressing action, and anti-obesity action and that are highly safe and contribute to maintenance and improvement of health.

In the present invention, promotion of lipid metabolism is preferably achieved by promoting fat burning (promoting fat consumption).

Suppression of fat accumulation encompasses fat accumulation prevention and/or fat accumulation reduction. In the present invention, fat is body fat and may refer to one or more of visceral fat, fat in the liver, and subcutaneous fat, but it preferably encompasses visceral fat and fat in the liver. In an embodiment, when the composition for promoting lipid metabolism or the like of the present invention is used to suppress fat accumulation, the composition is preferably used to suppress visceral fat accumulation or to suppress fat accumulation in the liver. Suppression of fat accumulation in the liver is also effective in preventing or ameliorating fatty liver.

As used herein, the term "prevention" and derivatives thereof encompasses prevention of symptom onset, delay of symptom onset, and decreased incidence of disease. The term "amelioration" or "ameliorating" encompasses relief of symptoms, suppression of progression of symptoms, cure, and complete recovery.

Isoxanthohumol can be an active ingredient that is added to products such as foods, beverages, pharmaceutical products, quasi-pharmaceutical products, feed, or feed additives to promote lipid metabolism, suppress fat accumulation, or prevent or ameliorate obesity. The degree of obesity prevention or amelioration can be evaluated by using the amount of body fat or body weight as an indicator. In an embodiment, isoxanthohumol can also be used as an active ingredient to suppress body weight increase.

As shown in the examples (described later), when mice fed on a high-fat diet were subjected to isoxanthohumol intake, the mice showed suppression of fat accumulation as compared to mice without isoxanthohumol intake. In addition, mice with isoxanthohumol intake also showed suppression of body weight increase as compared to mice without such intake. Thus, isoxanthohumol is effective, for example, in suppressing high-fat diet-induced fat accumulation (e.g., prevention of fat accumulation), preventing or ameliorating high-fat diet-induced obesity, and suppressing high-fat diet-induced body weight increase.

Known genes related to lipid metabolism include Cpt1 gene (gene encoding carnitine O-palmitoyltransferase type I), Acox1 gene (gene encoding acyl-CoA oxidase), Ucp1 gene (gene encoding mitochondrial uncoupling protein), Pgc-1α gene (gene encoding peroxisome proliferator-activated receptor γ coactivator), and the like.

Mitochondria are intracellular organelles found in eukaryotes. The main function of mitochondria is to supply energy.

Fatty acid β-oxidation is one of important metabolic pathways for extracting energy from fatty acids in mitochondria and peroxisomes. In mitochondria particularly, it refers to a metabolic pathway that produces acyl-CoA by oxidation of fatty acids and extracts Acetyl-CoA therefrom.

Carnitine O-palmitoyltransferase type I (Cpt1) plays a role of allowing acyl-CoA to pass through mitochondrial inner membranes by binding acyl-CoA to carnitine. Cpt1 is an enzyme that limits the rate of incorporation of acyl-CoA into mitochondria in fatty acid β-oxidation. Activation of Cpt1 increases fatty acid β-oxidation, and eventually, fat burning (Bulletin of Hiroshima Jogakuin University 61: 139-153). In peroxisome, acyl-CoA oxidase (Acox, ACO, or FAO) catalyzes initial oxidation reaction in fatty acid β-oxidation. Thus, promotion of expression of Cpt1a gene and Acox1 gene promotes fatty acid β-oxidation and consequently promotes fat burning.

As shown in the examples (described later), animals with isoxanthohumol intake showed an increase in expression level of Cpt1a gene and Acox1 gene in the liver. This suggests that isoxanthohumol promotes fatty acid β-oxidation, and which consequently promotes fat burning.

Mitochondrial uncoupling protein (UCP) is a protein that uncouples oxidative phosphorylation in the inner membrane of mitochondria which is an intracellular organelle and that has a function to dissipate energy as heat. In particular, analysis of the function of UCP1 that is expressed in the mitochondrial inner membrane of brown adipose tissue (BAT) has been progressing, and it has been reported that UCP1 has a function to promote thermogenesis induced by cold exposure or food intake (J Biol Chem. 2006 Oct. 20; 281 (42): 31894-908). Fatty acids are degraded in brown adipose tissue, and converted into heat by action of UCP1. Previous reports have proved that obese animals show decreased functions of UCP1 and that mice with artificially reduced UCP1 expression become obese while mice with high UCP1 expression lose weight (The 124th JAMS Symposium, Masayuki SAITO, 4. Role of UCP in the regulation of energy expenditure. Thus, an increase in the level of Ucp1 gene expression promotes thermogenesis and consequently promotes fat burning. Promotion of fat burning results in the fat accumulation-suppressing effect and the anti-obesity effect.

Peroxisome proliferator-activated receptor γ coactivator 1α (PGC-1α) is induced by increased sympathetic nerve activity, and is a transcriptional cofactor that positively regulates the synthesis of mitochondria. PGC-1α also positively regulates the expression of Ucp1 gene in adipose tissue, and functions to regulate lipid metabolism (PLoS One. 2013; 8 (5): e64123). Thus, promotion of expression of Pgc-1α gene in brown adipose tissue promotes expression of Ucp1 gene and consequently promotes fat burning.

As shown in the examples (described later), animals with isoxanthohumol intake showed an increase in expression level of Ucp1 gene and Pgc-1α gene in brown adipose tissue. This suggests that isoxanthohumol intake changes the expression of genes related to thermogenesis, resulting in promotion of fat burning.

Promotion of expression of genes such as Cpt1 gene and Ucp1 gene in mitochondria activates mitochondrial function. Thus, isoxanthohumol has mitochondrial function-activating action.

Thus, isoxanthohumol is effective in promoting fat burning. Isoxanthohumol can promote fat burning and consequently promote lipid metabolism. The composition for promoting lipid metabolism or the like of the present invention containing isoxanthohumol can be used to promote fat burning.

Isoxanthohumol can also promote fatty acid β-oxidation and thereby promote fat burning. Promotion of fatty acid β-oxidation can be achieved by promotion of expression of Cpt1 gene or Acox gene. The composition for promoting lipid metabolism or the like of the present invention containing isoxanthohumol can be used to promote lipid metabolism by promoting fatty acid β-oxidation.

Isoxanthohumol can also promote lipid metabolism by promoting thermogenesis. For example, it is possible to promote fat burning by promoting thermogenesis in brown adipose tissue. Thermogenesis in brown adipose tissue can be achieved, for example, by promotion of expression of Ucp1 gene or Pgc-1α gene in brown adipose tissue. In an embodiment of the present invention, the composition for promoting lipid metabolism or the like can be used to promote lipid metabolism by promoting thermogenesis in brown adipose tissue.

Isoxanthohumol can also promote fat burning by, for example, activating mitochondrial function. Thus, the composition for promoting lipid metabolism or the like of the present invention can also be used to promote lipid metabolism by activating mitochondrial function.

In an embodiment of the present invention, the composition for promoting lipid metabolism or the like is, for example, a composition for promoting lipid metabolism or the like which promotes lipid metabolism by promoting fatty acid β-oxidation or thermogenesis. In an embodiment, the composition for promoting lipid metabolism or the like is a composition for promoting lipid metabolism which promotes lipid metabolism by activating mitochondrial function.

Isoxanthohumol has lipid metabolism-promoting action and can suppress fat accumulation by the action, achieving an obesity-preventing or ameliorating effect. Thus, in an embodiment, the present invention provides a composition for anti-obesity for preventing or ameliorating obesity by promoting lipid metabolism (preferably, by promoting lipid metabolism by promoting fat burning). The composition for anti-obesity may be one for preventing or ameliorating obesity by promoting fat burning. In an embodiment, the present invention provides a composition for suppressing fat accumulation for suppressing fat accumulation by promoting fat burning. In an embodiment, the present invention provides a composition for promoting lipid metabolism for suppressing fat accumulation by promoting lipid metabolism; or a composition for promoting lipid metabolism for preventing or ameliorating obesity by promoting lipid metabolism. In an embodiment, the present invention also encompasses a composition for suppressing body weight increase which suppresses body weight increase by promoting lipid metabolism.

The composition for promoting lipid metabolism or the like of the present invention contains isoxanthohumol and promotes lipid metabolism, so that it can be used to suppress fat accumulation. The composition for promoting lipid metabolism or the like of the present invention shows lipid metabolism-promoting action and can also be used to prevent or ameliorate obesity or to suppress body weight increase. The composition for promoting lipid metabolism or the like of the present invention is applicable for either therapeutic use (medical use) or non-therapeutic use (non-medical use).

The composition for promoting lipid metabolism or the like of the present invention can be provided, for example, as a food or beverage (food or beverage composition), a pharmaceutical product (pharmaceutical product composition), a quasi-pharmaceutical product (quasi-pharmaceutical product composition), feed (feed composition), or a feed additive. The composition for promoting lipid metabolism or the like of the present invention is suitably as a composition for oral ingestion and is more suitable as a food or beverage. The composition for promoting lipid metabolism or the like of the present invention is suitably used, for example, as a food or beverage, pharmaceutical product, quasi-pharmaceutical product, feed, or feed additive to promote lipid metabolism, suppress fat accumulation, prevent or ameliorate obesity, or suppress body weight increase. The composition for promoting lipid metabolism or the like of the present invention may be a food or beverage, pharmaceutical product, quasi-pharmaceutical product, feed, or feed additive by itself to be used for the above purposes, or may be a raw material to be added thereto or a preparation. The composition for promoting lipid metabolism or the like of the present invention may be provided as an agent for example, but it is not limited thereto. The agent may be provided as a composition by itself or as a composition containing the agent.

The composition for promoting lipid metabolism or the like of the present invention may contain other ingredients, in addition to isoxanthohumol, as long as the effects of the present invention are not impaired. Examples of other ingredients include those that can be used in the later-described foods and beverages, pharmaceutical products, quasi-pharmaceutical products, feed, and feed additives. Products such as foods, beverages, pharmaceutical products, quasi-pharmaceutical products, feed, and feed additives can be produced by usual methods depending on ingredients.

The form of the composition for promoting lipid metabolism or the like of the present invention is not particularly limited. Non-limiting examples include powders, granules, pastes, solids, and liquids.

When the composition for promoting lipid metabolism or the like of the present invention is provided as a food or beverage, the food or beverage is not particularly limited. Examples include general foods and beverage, health foods, foods with function claims, foods for specified health uses, foods and beverages for the sick, and food additives. Examples of the health food and the foods with function claims can be used in various preparation forms such as fine granules, tablets, granules, powders, capsules, chewable tablets, syrups, liquids, and liquid foods.

When the composition for promoting lipid metabolism or the like is provided as a food or beverage, for example, isoxanthohumol may be used in combination with a material (e.g., a food or beverage raw material) that is usually used to produce foods or beverages.

The form of the food or beverage is not particularly limited, and may take various forms. Examples include beverages, confectionery, and supplements.

In an exemplary preferred embodiment, the composition for promoting lipid metabolism or the like of the present invention may be a beverage. The beverage may be a non-alcohol beverage or an alcohol beverage. Examples of the non-alcohol beverage include tea-based beverages, coffee beverages, non-alcoholic beer, carbonated beverages, functional beverages, fruit and/or vegetable-based beverages, lactic beverages, soy milk beverages, and flavored water.

When the composition for promoting lipid metabolism or the like of the present invention is a beverage, the beverage is preferably a tea-based beverage, coffee beverage, alcohol beverage, non-alcoholic beer, carbonated beverage, functional beverage, fruit and/or vegetable-based beverage, lactic beverage, soy milk beverage, or flavored water.

When the composition for promoting lipid metabolism or the like of the present invention is a tea-based beverage, preferred examples include black tea beverages and sugarless tea beverages. Examples of the sugarless tea beverage include green tea beverages, oolong tea beverages, barley tea beverages, brown rice tea beverages, adlay tea beverages, and sugarless black tea beverages.

When the composition for promoting lipid metabolism or the like of the present invention is a coffee beverage, preferred examples include packaged coffee beverages and liquid coffee.

Examples of the alcohol beverage include beer, beer-based beverages, and alcohol beverages other than the beer and beer-based beverages.

When the composition for promoting lipid metabolism or the like of the present invention is a beer-based beverage, preferred examples include low-malt beer or beer-like beverages.

When the composition for promoting lipid metabolism or the like of the present invention is an alcohol beverage other than the beer and beer-based beverages, preferred examples include shochu, shochu highballs, liqueurs, cocktail, spirits, and whiskies.

The term "non-alcoholic beer" as used herein refers to carbonated beverages with beer-like flavors of non-fermented, non-alcohol type, which are substantially free of alcohols. Here, the non-alcoholic beer does not exclude beverages containing a very trace amount (undetectable degree) of alcohol.

When the composition for promoting lipid metabolism or the like of the present invention is a carbonated beverage, preferred examples include cola-flavored beverages, clear carbonated beverages, ginger ale, fruit juice-based carbonated beverages, milk-containing carbonated beverages, and sugarless carbonated beverages.

When the composition for promoting lipid metabolism or the like of the present invention is a functional beverage, preferred examples include sports drinks, energy drinks, health-supporting beverages, and jelly drink pouches.

When the composition for promoting lipid metabolism or the like of the present invention is a fruit and/or vegetable-based beverage, preferred examples include 100% fruit juices, fruit-containing beverages, soft drinks with a low fruit juice content, pulp-containing fruit juices, and pulp-containing beverages.

When the composition for promoting lipid metabolism or the like of the present invention is a lactic beverage, preferred examples include milk, yogurt drinks, lactic acid bacteria beverages, and milk-containing soft drinks.

When the composition for promoting lipid metabolism or the like of the present invention is a soy milk beverage, preferred examples include soy milk and soybean beverages.

The form of the beverage is not particularly limited. Examples include packaged beverages. Packages for the packaged beverages are not particularly limited. Packages in any form and of any material may be used. For example, any of the following commonly used packages can be used: metal packages such as aluminum cans and steel cans; resin containers such as PET bottles; paper containers such as drink cartons; glass containers such as glass bottles; and wooden containers such as barrels. The beverage is filled in and sealed in any of these packages, whereby a packaged beverage can be obtained.

The food or beverage can be prepared, for example, by adding isoxanthohumol to a material used in the food or beverage production (e.g., a food or beverage raw material). A food or beverage containing isoxanthohumol can also be produced by adding and heating a hop extract in the food or beverage production. As described later, the food or beverage may contain γ-cyclodextrin and/or β-cyclodextrin in order to improve the solubility of isoxanthohumol.

When the composition for promoting lipid metabolism or the like of the present invention is provided as a pharmaceutical product or quasi-pharmaceutical product, the dosage (intake) form of the pharmaceutical product or quasi-pharmaceutical product may be an oral, enteral, or transmucosal administration or injection. Oral administration is preferred. Examples of dosage forms of preparation for oral administration includes liquids, tablets, powders, fine granules, granules, sugar-coated tablets, capsules, suspensions, emulsions, and chewable tablets. The dosage form of preparation for parenteral administration include injections, inhalations, infusions, suppositories, percutaneous absorption agents, nasal drops, eye drops, creams, gels, and lotions.

When the composition for promoting lipid metabolism or the like of the present invention is provided as a pharmaceutical product or quasi-pharmaceutical product, for example, isoxanthohumol can be used in combination with pharmaceutically or quasi-pharmaceutically acceptable carriers, optional additives, or the like. Such carriers, additives, and the like are not limited as long as they are pharmaceutically or quasi-pharmaceutically acceptable. Examples include excipients, binders, disintegrants, lubricants, antioxidants, and colorants. One or more of these can be used.

When the composition for promoting lipid metabolism or the like of the present invention is provided as a pharmaceutical product or quasi-pharmaceutical product, the production method of such a product is also not particularly limited, and such a product may be produced by a method known per se. For example, isoxanthohumol may be added in the production of pharmaceutical products or quasi-pharmaceutical products. Pharmaceutical products or quasi-pharmaceutical products containing isoxanthohumol can also be produced by adding and heating a hop extract in the production of pharmaceutical products or quasi-pharmaceutical products.

When the composition for promoting lipid metabolism or the like of the present invention is provided as a food or beverage, pharmaceutical product, or quasi-pharmaceutical product, the isoxanthohumol content is not particularly limited and can be determined depending on the form or the like of the product. For example, the isoxanthohumol content is preferably 0.0001% by weight or more and 90% by weight or less in the composition for promoting lipid metabolism or the like. In an embodiment, the isoxanthohumol content is preferably 0.0001 to 90% by weight, more preferably 0.0003 to 90% by weight, still more preferably 0.001 to 50% by weight, particularly preferably 0.003 to 30% by weight, in the composition for promoting lipid metabolism or the like.

For example, when the composition for promoting lipid metabolism or the like is provided as a beverage, the isoxanthohumol concentration is preferably 0.001 to 0.050% by weight, more preferably 0.003 to 0.030% by weight, in the beverage. For example, in the case of a 200- to 500-mL packaged beverage, the isoxanthohumol content is preferably 5 to 100 mg, more preferably 15 to 60 mg, in the beverage.

When the composition for promoting lipid metabolism or the like of the present invention is used as a food or beverage, pharmaceutical product, or quasi-pharmaceutical product, the isoxanthohumol dose or intake may be any amount that can achieve the lipid metabolism-promoting effect, fat accumulation-suppressing effect, or the like, and may be suitably set depending on subject conditions, body weight, age, sex, or other factors. For example, in the case of a human adult, the amount of isoxanthohumol is preferably 5 to 200 mg, more preferably 5 to 100 mg, still more preferably 15 to 60 mg, per 60 kg body weight per day. Isoxanthohumol in the above amount is preferably orally ingested or orally administered at once or in several portions per day.

When the composition for promoting lipid metabolism or the like of the present invention is provided as feed or a feed additive, isoxanthohumol is added to feed or a feed additive. Examples of the feed include livestock feed for animals such as cows, pigs, chickens, sheep, and horses; feed for small animals such as rabbits, rats, and mice; and pet food for animals such as dogs, cats, and birds. Feed can be produced by a usual method, for example, by adding feed raw materials commonly used for these animals and desired optional additives to isoxanthohumol. The isoxanthohumol content in the feed or feed additive is not particularly limited, and for example, it is preferably 0.0001% by weight or more and 90% by weight or less in the feed or feed additive. In an embodiment, the isoxanthohumol content is preferably 0.0001 to 90% by weight, more preferably 0.0003 to 90% by weight, still more preferably 0.001 to 50% by weight, particularly preferably 0.003 to 30% by weight.

The composition for promoting lipid metabolism or the like of the present invention shows lipid metabolism-promoting action, fat accumulation-suppressing action, anti-obesity action, and body weight increase-suppressing action. Thus, the composition is effective, for example, in waist circumference reduction, waist circumference maintenance, slim body maintenance, suppression of body fat accumulation, body fat reduction, suppression of visceral fat accumulation, visceral fat reduction, weight loss (weight reduction), diet, or metabolic syndrome prevention or amelioration, and can be used for any of these purposes. For example, the composition for suppressing fat accumulation is effective to obtain one or more of the actions selected from suppression of body fat accumulation, body fat reduction, suppression of visceral fat accumulation, visceral fat reduction, suppression of fat accumulation in the liver, fat reduction in the liver, and metabolic syndrome prevention or amelioration.

The composition for promoting lipid metabolism or the like of the present invention may be labeled with function claims based on the lipid metabolism-promoting action or fat accumulation-suppressing action, or may be labeled with function claims based on the anti-obesity action or body weight increase-suppressing action.

The composition for promoting lipid metabolism or the like of the present invention may be labeled with one or more of the following function claims, for example: "anti-obesity", "obesity prevention", "obesity amelioration", "waist circumference reduction", "waist circumference maintenance", "slim body maintenance", "suppression of body fat accumulation", "body fat reduction", "suppression of visceral fat accumulation", "visceral fat reduction", "suppression of fat accumulation in the liver", "fat reduction in the liver", "weight loss", "weight reduction", "diet", "fat burning", "fat consumption", "lipid metabolism", "mitochondrial function", "thermogenesis", "basal metabolism", "metabolic function", "metabolic capacity", "metabolic syndrome prevention", and "metabolic syndrome amelioration".

In addition, for example, the composition for anti-obesity and the composition for suppressing fat accumulation of the present invention may be labeled with one or more of the following function claims: "anti-obesity", "obesity prevention", "obesity amelioration", "waist circumference reduction", "waist circumference maintenance", "slim body maintenance", "suppression of body fat accumulation", "body fat reduction", "suppression of visceral fat accumulation", "visceral fat reduction", "weight loss", "weight reduction", "diet", "metabolic syndrome prevention", and "metabolic syndrome amelioration". In an embodiment, when the composition for suppressing fat accumulation of the present invention is labeled, it may be labeled with one or more of the following function claims: "suppression of body fat accumulation", "body fat reduction", "suppression of visceral fat accumulation", "visceral fat reduction", "metabolic syndrome prevention", and "metabolic syndrome amelioration". The composition for promoting lipid metabolism may be labeled with one or more of the following function claims: "fat burning", "fat consumption", "lipid metabolism", "mitochondrial function", "thermogenesis", "basal metabolism", "metabolic function", and "metabolic capacity"; or one or more of the following function claims: "fat burning", "fat consumption", and "lipid metabolism".

In an embodiment of the present invention, the composition for promoting lipid metabolism or the like of the present invention is preferably a food or beverage with the function claim(s). The labels indicating the function claims may be labels indicating use for obtaining these functions.

A subject that consumes or is administered with the composition for promoting lipid metabolism or the like of the present invention is preferably an animal, more preferably a vertebrate, still more preferably a mammal (a human or non-human mammal). In particular, the subject that consumes or is administered with the composition for promoting lipid metabolism or the like of the present invention is preferably a human. The composition for promoting lipid metabolism or the like of the present invention can be suitably used by a subject requiring promotion of lipid metabolism, suppression of fat accumulation, or obesity prevention or amelioration. The composition for promoting lipid metabolism or the like of the present invention can be suitably used by a subject wanting promotion of lipid metabolism, suppression of fat accumulation, or obesity prevention or amelioration, for example. The composition for promoting lipid metabolism or the like of the present invention can also be used by a subject requiring or wanting body weight increase suppression.

The present invention also encompasses a method of promoting lipid metabolism, including administering isoxanthohumol. The present invention also encompasses a method of suppressing fat accumulation, including administering isoxanthohumol. The present invention also encompasses a method of preventing or ameliorating obesity, including administering isoxanthohumol. The method of preventing or ameliorating obesity is preferably a method including administering isoxanthohumol to promote lipid metabolism.

The present invention also encompasses a method of suppressing body weight gain, including administering isoxanthohumol.

In the above methods, a subject is administered with isoxanthohumol in an amount capable of providing the lipid metabolism-promoting effect (e.g., fat burning-promoting effect), fat accumulation-suppressing effect, or the like (such an amount can also be referred to as "effective amount"). A preferred dose of isoxanthohumol, a preferred subject to be administered with isoxanthohumol, and the like are the same as described for the composition for promoting lipid metabolism or the like of the present invention. Administration is preferably oral administration, for example. Isoxanthohumol may be administered directly, or may be administered as a composition containing isoxanthohumol. For example, the composition for promoting lipid metabolism or the like of the present invention described above may be administered. The method may be a therapeutic method or a non-therapeutic method. The "non-therapeutic" is a concept that does not include medical activities, i.e., a concept that does not include methods of surgery, therapy or diagnosis of humans.

The present invention also encompasses the following uses:

use of isoxanthohumol in promoting lipid metabolism;
use of isoxanthohumol in suppressing fat accumulation;
use of isoxanthohumol in suppressing body weight gain; and
use of isoxanthohumol in preventing or ameliorating obesity. In the use to prevent or ameliorate obesity, isoxanthohumol is preferably used to prevent or ameliorate obesity by promoting lipid metabolism.

Isoxanthohumol is also suitably used to promote fat burning.

The use is preferably use in an animal (preferably mammal). The use may be therapeutic or non-therapeutic use.

The amount (dose) and the like of isoxanthohumol are the same as those described above for the composition for promoting lipid metabolism or the like of the present invention. Isoxanthohumol may be used as is or may be used as a composition containing isoxanthohumol. For example, the composition for promoting lipid metabolism or the like of the present invention may be used.

Isoxanthohumol can also be used to produce foods, beverages, pharmaceutical products, quasi-pharmaceutical products, feed, feed additives, and the like, which are used for the above purposes. In an embodiment, the present invention also encompasses use of isoxanthohumol in producing the composition for promoting lipid metabolism, the composition for suppressing fat accumulation, or the composition for anti-obesity.

In the method and the use, promotion of lipid metabolism and suppression of fat accumulation are the same as described above. For example, promotion of lipid metabolism is preferably achieved by promoting fat burning. Promotion of lipid metabolism may be achieved by promoting fatty acid β-oxidation or thermogenesis. Promotion of lipid metabolism may be achieved by activating mitochondrial function.

Suppression of fat accumulation is preferably suppression of visceral fat accumulation or fat accumulation in the liver. Isoxanthohumol is preferably used to suppress fat accumulation by promoting fat burning.

The present invention also encompasses the following method of improving the solubility of isoxanthohumol and the like.

<1> Method for improving the solubility of isoxanthohumol, the method including adding at least one selected from the group consisting of a hop extract, β-cyclodextrin, and γ-cyclodextrin, to a composition containing isoxanthohumol <2> Use of at least one selected from the group consisting of a hop extract, β-cyclodextrin, and γ-cyclodextrin, for the improvement of the solubility of isoxanthohumol <3> An isoxanthohumol solubility improver containing, as an active ingredient, at least one selected from the group consisting of a hop extract, β-cyclodextrin, and γ-cyclodextrin The solubility is preferably solubility in water (water solubility). The hop extract, β-cyclodextrin, and γ-cyclodextrin show an isoxanthohumol solubility-improving effect. Any of these may be used alone or in combination of two or more thereof.

The hop extract can be a water extract of hop cones, its concentrate, dried matter, or the like.

In view of a high isoxanthohumol solubility-improving effect, use of γ-cyclodextrin is preferred. As shown in the examples (described later), for example, when 0.2% (w/v) γ-cyclodextrin was added under ice cooling conditions to an aqueous solution containing isoxanthohumol, the solubility of the isoxanthohumol was about 5 times higher than that of isoxanthohumol dissolved in an aqueous solution without γ-cyclodextrin. When 1.0% (w/v) γ-cyclodextrin was added under the above conditions to an aqueous solution containing isoxanthohumol, the solubility of the isoxanthohumol was about 18 times higher than that of isoxanthohumol dissolved in an aqueous solution without γ-cyclodextrin.

When at least one selected from the group consisting of a hop extract, β-cyclodextrin, and γ-cyclodextrin is added to a composition containing isoxanthohumol, the amount is not limited as long as the solubility-improving effect can be achieved. In order to improve the solubility of isoxanthohumol, the amount of β-cyclodextrin is, for example, preferably 0.1% by weight or more, more preferably 0.2% by weight or more, still more preferably 0.2 to 1.0% by weight, in the composition. The amount of γ-cyclodextrin is preferably 0.1% by weight or more, more preferably 0.2% by weight or more, still more preferably 0.2 to 1.0% by weight, in the composition.

In order to improve the solubility of isoxanthohumol, the amount of β-cyclodextrin in terms of weight ratio relative to isoxanthohumol (β-cyclodextrin/isoxanthohumol) is preferably 10 to 3000, more preferably 38 to 1587. As for the amount of γ-cyclodextrin, the weight ratio of γ-cyclodextrin relative to isoxanthohumol (γ-cyclodextrin/isoxanthohumol) is preferably 10 to 3000, more preferably 17 to 1587.

The present invention also encompasses the following composition:

a composition containing: (A) at least one selected from the group consisting of β-cyclodextrin and γ-cyclodextrin; and (B) isoxanthohumol.

In order to improve the solubility of isoxanthohumol, a preferred range of the compounding ratio of (A) and (B) is as described above. The composition containing (A) and (B) may be used as the composition for promoting lipid metabolism or the like of the present invention.

EXAMPLES

The following provides examples that more specifically describe the present invention. The present invention is not limited to these examples.

A series of animal experiments was performed based on a plan approved by the relevant chief through evaluation of the in-house animal experiment committee, in compliance with the animal welfare management laws and other related laws and regulations.

Preparation Example 1

Preparation of Xanthohumol and Isoxanthohumol

Isoxanthohumol and xanthohumol were isolated and purified from a hop extract (Asama Chemical. Co., Ltd.) by the following method. Specifically, using a hop extract as a raw material, isoxanthohumol and xanthohumol were purified by normal-phase column chromatography, reverse phase column chromatography, and preparative HPLC, and the purity was determined to be 95% or higher by HPLC analysis. For HPLC analysis, a Develosil C30-UG-5 column (Nomura Chemical Co., Ltd.) was used, and the detector wavelength to measure UV absorption was 280 nm (isoxanthohumol) or 350 nm (xanthohumol).

The obtained isoxanthohumol and xanthohumol were used as standard samples (both having a purity of 95% or higher) in the following experiments.

Example 1

Evaluation Regarding Anti-Obesity Action of Isoxanthohumol in High-Fat Diet Model The effect of isoxanthohumol on body weight increase and fat accumulation associated with high-fat diet was studied by the following procedure.

(Group Structure)

Table 1 shows groups (group name, basic feed, test substance, and dose of the test substance) in the present test.

In the table, "Regular diet" is control diet "D12450J" (product name, Research Diets); "60 kcal % High-fat diet" is very high-fat diet "D12492" (product name, Research Diets); and "Catechins" is a preparation "Polyphenon 70A" (product name, Mitsui Norin Co., Ltd.). Xanthohumol and isoxanthohumol were the standard samples (purity of 95% or higher) obtained in Preparation Example 1. The "Dose" in the table indicates the dose (mg) of the test substance per day per kg body weight.

TABLE 1

| Group No. | Group name | Basic feed | Test substance | Dose (mg/kg/day) |
|---|---|---|---|---|
| 1 | Regular diet | Regular diet | None | 0 |
| 2 | High-fat diet | 60 kcal % High-fat diet | None | 0 |
| 3 | Catechins (positive control) | 60 kcal % High-fat diet | Catechins | 300 |
| 4 | Xanthohumol medium dose | 60 kcal % High-fat diet | Xanthohumol | 60 |
| 5 | Isoxanthohumol low dose | 60 kcal % High-fat diet | Isoxanthohumol | 20 |
| 6 | Isoxanthohumol medium dose | 60 kcal % High-fat diet | Isoxanthohumol | 60 |
| 7 | Isoxanthohumol high dose | 60 kcal % High-fat diet | Isoxanthohumol | 180 |

(Evaluation Items)

The main evaluation items were the body weight and the fat weight (fat around epididymis, fat around kidney/posterior abdominal wall, and fat around mesentery) of each individual (each item was measured on the last day: day 55 of administration).

(Acclimatization and Grouping)

Mice (C57BL/6J, male, 7 weeks of age, CLEA Japan, Inc.) were purchased, and they were quarantine and acclimatized for one week. Then, animals were selected based on changes in body weight from animals that showed no abnormalities in observation of general conditions. The selected animals were divided into groups (n=8 in each group) in the group structure shown in Table 1 by the stratified continuous randomization method based on body weight at the end of the acclimatization period. They were fed with free access to specific basic feed and water.

(Method for Administering Test Substance)

The test substance was orally administered once per day for eight weeks.

The test substance was administered until day 55, with the dosing start date defined as day 0. The duration was regarded as an administration period. During the administration period, the feed was completely replaced with a frequency of twice a week. The volume of a dosing solution was 10 mL/kg, and the amount of the test substance and the volume of the solution were calculated based on the latest body weight on the administration date.

(Tissue Extraction and Weight Measurement)

After the administration period, adipose tissue (fat around epididymis, fat around kidney/posterior abdominal wall, fat around mesentery) was extracted, and the weight was measured.

(Statistical Analysis)

Statistical analysis was performed as follows. Specifically, the average and standard error were calculated for body weight and fat weight in each group. Statistical processing was performed using Microsoft Office Excel 2003, and significant difference was tested between the regular diet group and the high-fat diet group and between the high-fat diet group and the groups excluding the regular diet group. As a statistical method, the homogeneity of variance was tested using the F-test. Student's T-test was used for homoscedasticity, and Aspin-Welch t-test was used for heteroscedasticity.

(Results)

FIGS. 1 to 4 show average body weights and fat weights (fat around epididymis, fat around kidney/posterior abdominal wall, and fat around mesentery) of each group (n=8). In FIGS. 1 to 4 XN is xanthohumol, and IX is isoxanthohumol. The results shown in FIGS. 1 to 4 are results measured on the last day (day 55 of days of administration) (significant differences are relative to the high-fat diet group).

Figure 1:
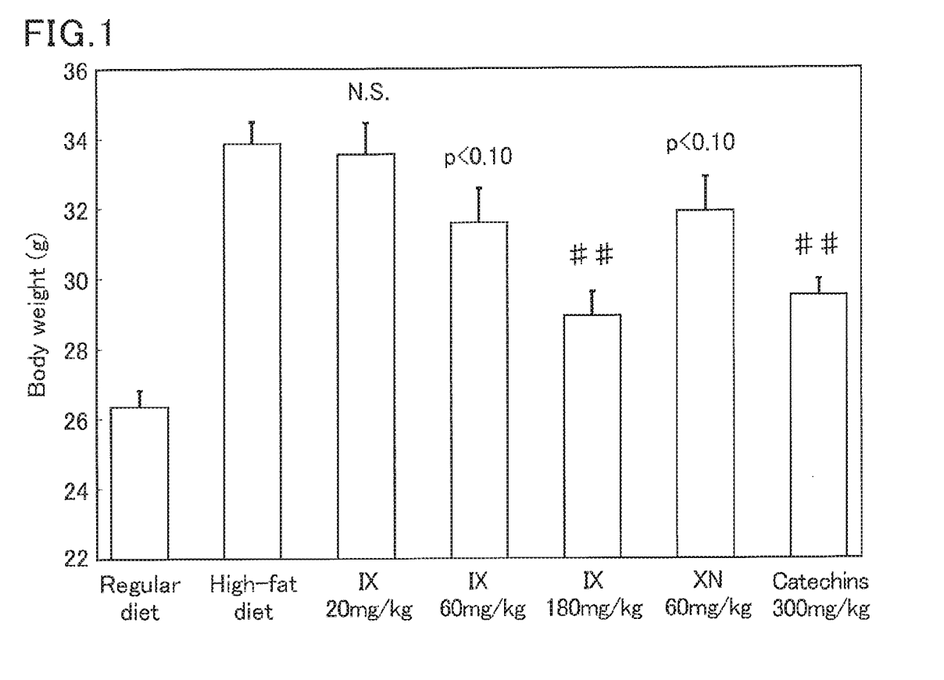
FIG. 1 is a graph showing the average body weight of each group (#: $p<0.05$, ##: $p<0.01$, N.S.: $p\geq 0.10$ vs. high-fat diet group).

FIG. 1 is a graph showing the average body weight of each group (#: $p<0.05$, ##: $p<0.01$, N.S.: $p≥0.10$ vs. high-fat diet group).

Figure 2:
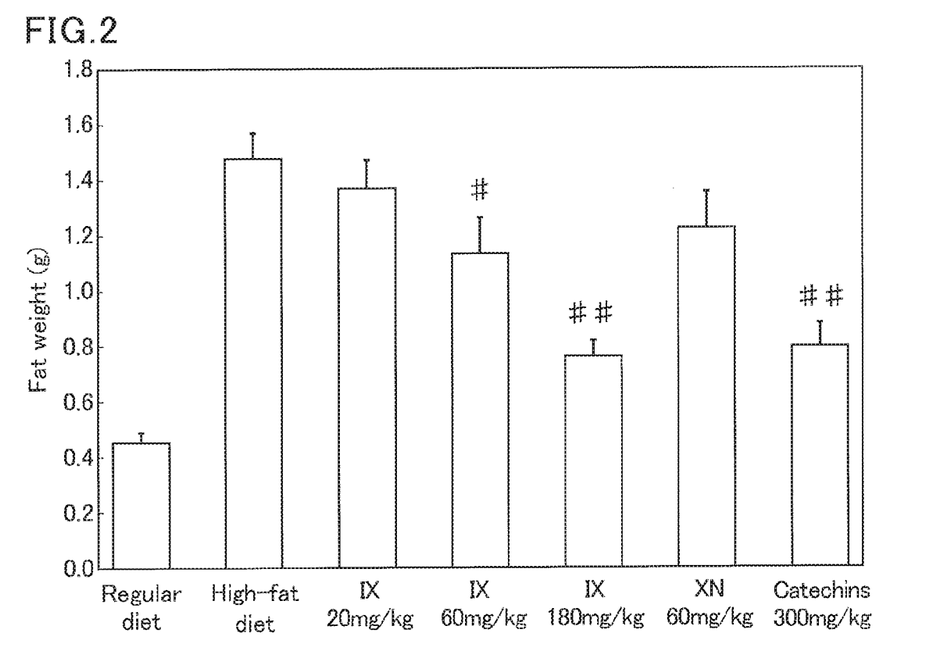
FIG. 2 is a graph showing the average fat weight around epididymis of each group (#: $p<0.05$, ##: $p<0.01$ vs. high-fat diet group).

FIG. 2 is a graph showing the average fat weight around epididymis of each group (#: $p<0.05$, ##: $p<0.01$ vs. high-fat diet group).

Figure 3:
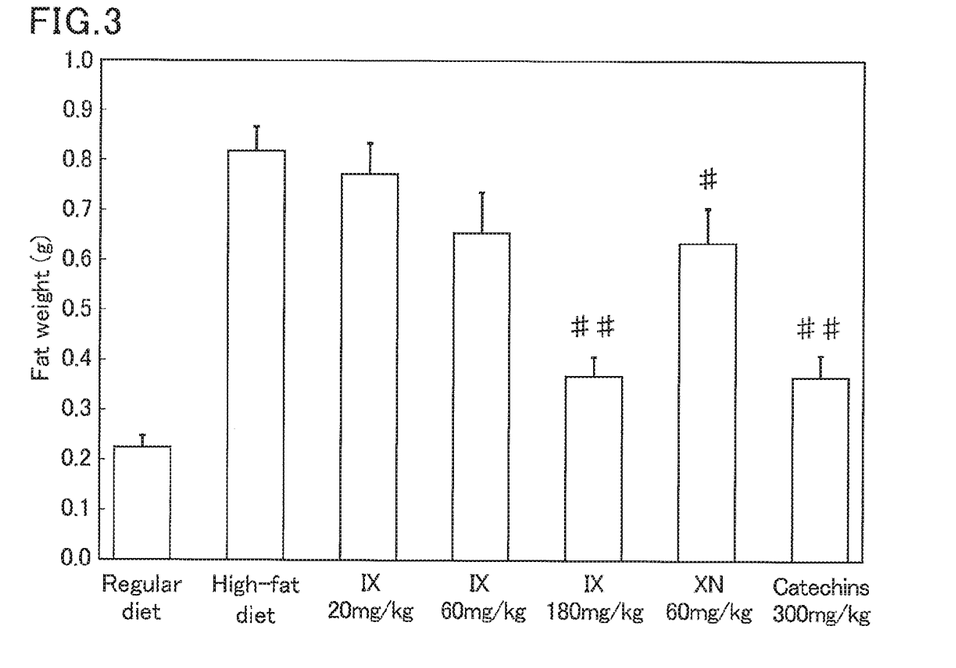
FIG. 3 is a graph showing the average fat weight around kidney and around posterior abdominal wall of each group (#: $p<0.05$, ##: $p<0.01$ vs. high-fat diet group).

FIG. 3 is a graph showing the average fat weight around kidney and around posterior abdominal wall of each group (#: $p<0.05$, ##: $p<0.01$ vs. high-fat diet group).

Figure 4:
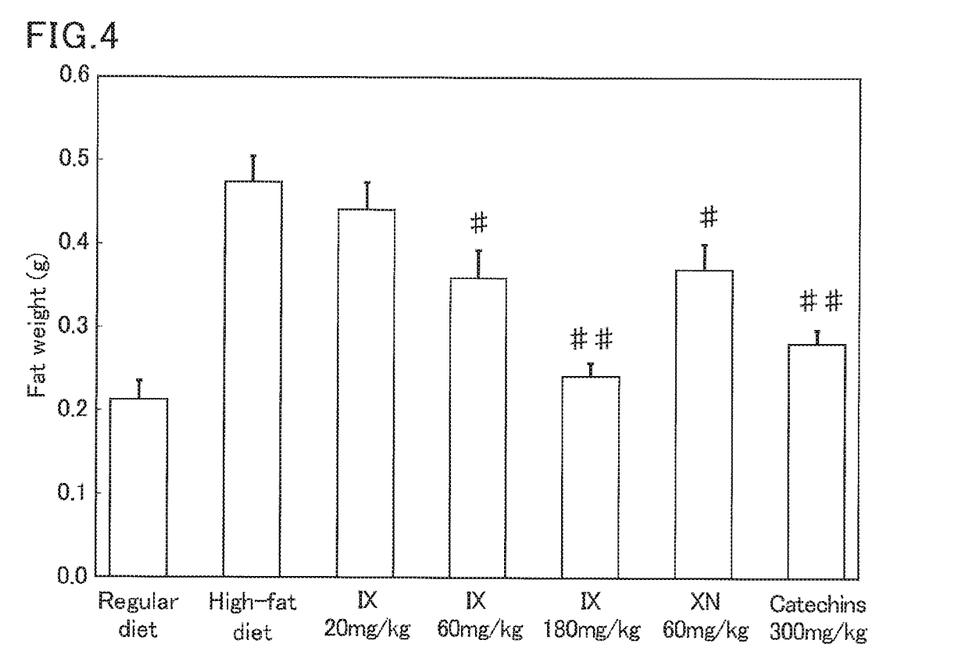
FIG. 4 is a graph showing the average fat weight around mesentery of each group (#: $p<0.05$, ##: $p<0.01$ vs. high-fat diet group).

FIG. 4 is a graph showing the average fat weight around mesentery of each group (#: $p<0.05$, ##: $p<0.01$ vs. high-fat diet group).

As compared to the high-fat diet group, the isoxanthohumol medium-dose group (60 mg/kg) tended to have a low body weight, and the fat weights around epididymis and mesentery were significantly low. The results show that the body weight and all the fat weights were significantly low in the isoxanthohumol high-dose group (180 mg/kg). The average body weight of the isoxanthohumol medium-dose group (60 mg/kg) was equivalent to that of the xanthohumol medium-dose group (60 mg/kg). The isoxanthohumol high-dose group (180 mg/kg) showed a better result in the average body weight than the catechins group (300 mg/kg). This shows that the anti-obesity action and fat accumulation-suppressing action of isoxanthohumol are as strong as those of xanthohumol, and are stronger than those of catechins.

Example 2

Measurement of Triglyceride (TG) Content in Liver

The neutral fat content (also referred to as "triglyceride content" or "TG content") in the liver was measured using the liver extracted in Example 1. Specifically, the extracted liver was cut to obtain a section of about 30 mg, and 1 mL of a mixed solution containing methanol (Nacalai Tesque, Inc.) and chloroform (Nacalai Tesque, Inc.) at a ratio of 1:1 was added to the section which was then crushed with a bead beater, whereby triglyceride in the liver was extracted. After centrifugation (12000 g, for 15 minutes), the supernatant was collected, the solution was distilled off, and isopropanol was added for re-dissolution, whereby a sample was prepared. The triglyceride content in the sample was measured using Triglyceride E Test Wako (Wako), and the triglyceride content (mg/g) in the liver per unit weight was calculated. The data was presented as average f standard error. Student's t-test was used as a statistical test, and a difference with $p<0.05$ was considered significant.

(Results)

Figure 5:
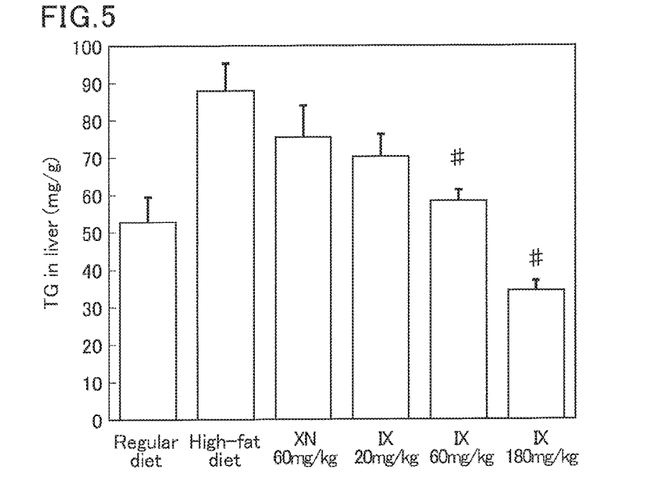
FIG. 5 is a graph showing the triglyceride content (mg/g) in the liver per unit weight of each group (#: $p<0.05$ vs. high-fat diet group).

FIG. 5 shows the triglyceride content (mg/g) in the liver per unit weight of each group (#: p<0.05 vs. high-fat diet group). In FIG. 5, XN is xanthohumol and IX is isoxanthohumol. The measurement results of triglyceride (TG) content in the liver show that the neutral fat content in the liver in the isoxanthohumol-administered group was significantly lower than that in the high-fat diet group, and the action of isoxanthohumol was stronger than that of xanthohumol. In other words, isoxanthohumol was confirmed to have neutral fat accumulation-suppressing action in the liver.

Example 3

Effect of Isoxanthohumol Intake on Fat Burning

Figure 6:
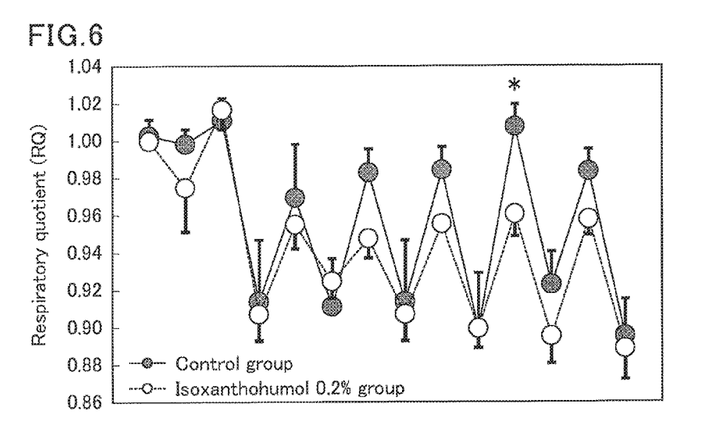
FIG. 6 is a graph plotting the respiratory quotient (RQ) of a control group and an isoxanthohumol 0.2% group.

The effect of isoxanthohumol intake on fat burning was studied by the following procedure using a respirometer "Oxymax" (Bio Research Center Co., Ltd.).
(Group Structure, Acclimatization, and Grouping)
As for the group structure, there were two groups: a control group and an isoxanthohumol 0.2% group. Eight mice (C57BL/6J, male, 14 weeks of age, CLFA Japan, Inc.) were purchased and acclimatized for about one week. Then, the mice were divided into the control group and the isoxanthohumol 0.2% group (n=4 in each group) by the stratified continuous randomization method based on body weight. Control diet "D12450J" (Research Diets) was used as basic feed. During the test period, the control group was fed with the basic feed, and the isoxanthohumol 0.2% group was fed with mixed feed of the basic feed and the test substance (isoxanthohumol obtained in Preparation Example 1) at a weight ratio of 0.2% relative to the basic feed.
(Operation During Test)
The test period (a period in which the test substance was ingested, and breath analysis was performed) was seven days. During the test period, the mice were fed with free access to feed and water in a test chamber. Using Oxymax (Bio Research Center Co., Ltd.), the oxygen consumption ($VO_2$) and the carbon dioxide output ($VCO_2$) of each individual were measured over time and recorded.
(Analysis Method)
The respiratory quotient (RQ) was calculated using the following formula 1 from the oxygen consumption ($VO_2$) and the carbon dioxide output ($VCO_2$) at each point.

Respiratory quotient (RQ)=Carbon dioxide output ($VCO_2$)/Oxygen consumption ($VO_2$)    (Formula 1)

The respiratory quotient (RQ) indicates a lower value when the rate of fat burning (fat consumption) increases. For the respiratory quotient (RQ) at each point, the average and standard error were calculated for the light period (7 a.m. to 7 p.m.) and the dark period (7 p.m. to 7 a.m.), and the calculated values were plotted on the vertical axis of a graph. FIG. 6 shows the graph plotting the respiratory quotient (RQ) of the control group and the isoxanthohumol 0.2% group (the horizontal axis shows the evaluation period sequentially from the dark period on day 1 to the light period on day 7). In the graph of FIG. 6, black indicates the control group, and white indicates the isoxanthohumol 0.2% group.
(Statistical Analysis)
Statistical analysis was performed using Microsoft Office Excel 2003. Significant difference was tested by Student's t-test (significant level: 5%) between the control group and the isoxanthohumol 0.2% group in each period (*: p<0.05).

(Results)
The isoxanthohumol 0.2% group showed a lower respiratory quotient (RQ) than the control group. In other words, the results show that the isoxanthohumol intake increases fat burning (fat consumption).

Example 4

Effect of Isoxanthohumol Intake on Expression of Gene Relating to Fat Burning

Using the high-fat diet model, the effect of isoxanthohumol intake on expression of a gene related to fat burning was studied by the following procedure.
(Group Structure, Acclimatization, and Grouping)
Thirty-two mice (C57BL/6J, male, 8 weeks of age, CLEA Japan, Inc.) were purchased and acclimatized for about one week. Then, the mice were divided into groups (n=8 in each group) in the group structure shown in Table 2 by the stratified continuous randomization method based on body weight. Table 2 shows a group structure (group name, basic feed, test substance, and dose of the test substance) in the present test. In Table 2, "Regular diet" is control diet "D12450J" (Research Diets), and "60 kcal % High-fat diet" is very high-fat diet "D12492" (Research Diets). Isoxanthohumol as the test substance was the standard sample (purity of 95% or higher) obtained in Preparation Example 1. The "Dose" in the table indicates the dose (mg) of the test substance per day per kg body weight.

TABLE 2

| Group No. | Group name | Basic feed | Test substance | Dose (mg/kg/day) |
|---|---|---|---|---|
| 1 | Regular diet (Control) | Regular diet | None | 0 |
| 2 | High-fat diet (HF) | 60 kcal % High-fat diet | None | 0 |
| 3 | Isoxanthohumol (IX) 30 mg/kg | 60 kcal % High-fat diet | Isoxanthohumol | 30 |
| 4 | Isoxanthohumol (IX) 60 mg/kg | 60 kcal % High-fat diet | Isoxanthohumol | 60 |

(Operation During Test Period)
The test period was 14 days. During the test period, a solvent and the test substance were orally administered once per day. For a dosing solution, a 0.5% aqueous solution of sodium carboxymethylcellulose (CMC) was used as a solvent. The volume of the dosing solution was 10 mL/kg. The amount of the test substance and the volume of the solution were calculated based on the latest body weight on the administration date. The mice were fed with free access to feed and water.
(Tissue Extraction)
The liver and brown adipose tissue were extracted on the last day of the test period.
(Study of Expression of Genes Related to Lipid Metabolism)
Using the extracted liver and brown adipose tissue, the effect of isoxanthohumol intake on expression of multiple genes related to lipid metabolism was studied. This study allows searching for functionality related to lipid metabolism of isoxanthohumol. Specifically, RNAs were extracted from the liver and brown adipose tissue cells using Qiazol (product name, QIAGEN), and the RNAs were purified using RNeasy Mini Kit (product name, QIAGEN). Then, cDNAs were synthesized using High-Capacity cDNA Reverse Transcription Kit (product name, Life Technologies Corporation), and the expression levels of genes shown in Table 3 were examined by quantitative PCR (TaqMan probe method) using Fast Universal PCR Master Mix (product name, Life Technologies Corporation). Table 3 also shows the primers used (product numbers, Thermo Fisher Scientific Inc.). Analysis was performed using the comparative Ct method with 18S rRNA gene as an internal standard gene, and the gene expression level was calculated by correlation with 18S rRNA gene. FIGS. 7 to 10 show the results. The gene expression levels were indicated relative to the regular diet group (control, group without addition of the test substance). The data was presented as average±standard error. Student's t-test was used as a statistical test, and a difference with $p<0.05$ was considered significant.

TABLE 3

| Abbreviation | Formal name | Primer product no. (TaqMan) |
|---|---|---|
| Acox1 | Acyl-CoA oxidase | Mm01246834_m1 |
| Cpt1a | Carnitine palmitoyltransferase 1a | Mm01231183_m1 |
| Ucp1 | Uncoupling protein-1 | Mm01244861_m1 |
| Pgc-1α | Peroxisome proliferator-activated receptor gamma coactivator 1-alpha | Mm01208835_m1 |

Figure 7:
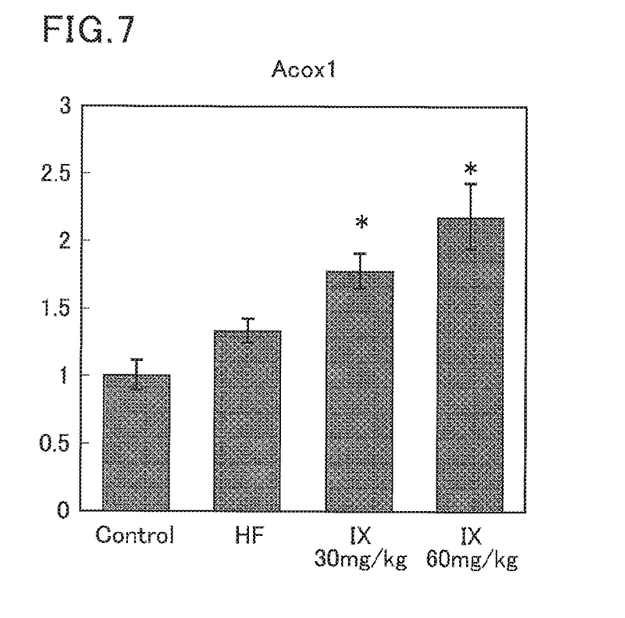
FIG. 7 shows the relative expression level of Acox1 gene in the liver (value relative to the regular diet group (control) taken as 1) (*: $p<0.05$).

FIG. 7 shows the relative expression level of Acox1 gene in the liver (value relative to the regular diet group (control) taken as 1) (*: $p<0.05$).

Figure 8:
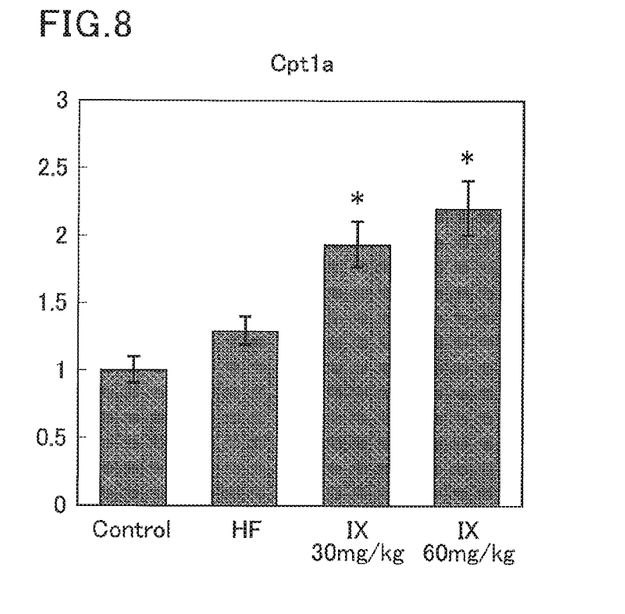
FIG. 8 shows the relative expression level of Cpt1a gene in the liver (value relative to the regular diet group (control) taken as 1) (*: $p<0.05$).

FIG. 8 shows the relative expression level of Cpt1a gene in the liver (value relative to the regular diet group (control) taken as 1) (*: $p<0.05$).

Figure 9:
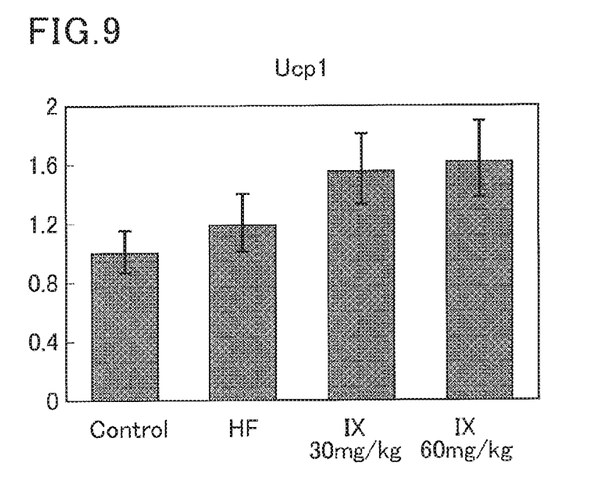
FIG. 9 shows the relative expression level of Ucp1 gene in brown adipose tissue (value relative to the regular diet group (control) taken as 1) (*: $p<0.05$).

FIG. 9 shows the relative expression level of Ucp1 gene in brown adipose tissue (value relative to the regular diet group (control) taken as 1) (*: $p<0.05$).

Figure 10:
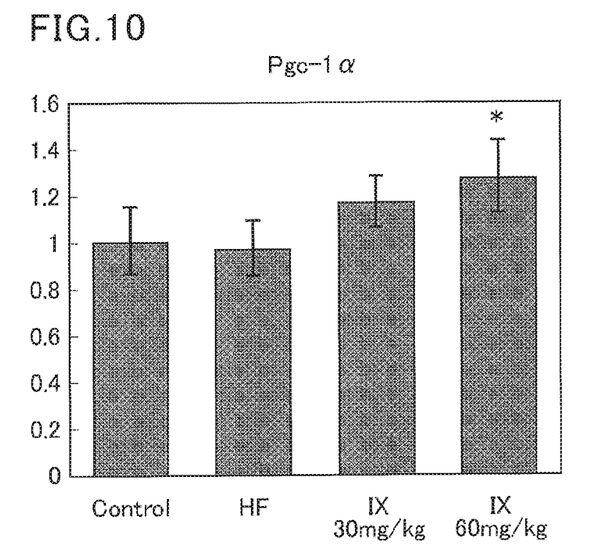
FIG. 10 shows the relative expression level of Pgc-1α gene in brown adipose tissue (value relative to the regular diet group (control) taken as 1) (*: $p<0.05$).

FIG. 10 shows the relative expression level of Pgc-1α gene in brown adipose tissue (value relative to the regular diet group (control) taken as 1) (*: $p<0.05$).

The data was presented as average±standard error. Student's t-test was used as a statistical test, and a difference with $p<0.05$ was considered significant.

In FIGS. 7 to 10, HF is the high-fat diet group, and IX is the isoxanthohumol-administered group.

(Results)

The above studies show a significant increase in the gene expression levels of Cpt1a gene and Acox1 gene in the liver by isoxanthohumol intake. This suggests that fatty acid β-oxidation has increased, resulting in an increase in fat burning. The above studies also show a significant increase in Pgc-1α gene in the brown adipose tissue by isoxanthohumol intake. This shows that the genes related to thermogenesis have fluctuated, resulting in an increase in fat burning.

Test Example 1

Evaluation of Solubility of Xanthohumol and Isoxanthohumol Under Ice Cooling Conditions The solubility of each of the standard samples of xanthohumol and isoxanthohumol in water (Experiment A) and various solvents (Experiment B) under ice cooling conditions was studied to evaluate the suitability for beverage applications. Xanthohumol and isoxanthohumol were the standard samples obtained in Preparation Example 1 (purity of 95% or higher).

(Procedure)

(Experiment A: Study of Solubility of Xanthohumol and Isoxanthohumol in Water)

A sample containing distilled water and xanthohumol or isoxanthohumol having a weight corresponding to 0.2% (w/v) of the distilled water was prepared, and each standard sample was allowed to dissolve in distilled water as much as possible by stirring in a vortex mixer for 10 seconds or longer and shaking for about 60 minutes under ice cooling conditions. Further, centrifugation was performed (12,000 rpm, 4° C., for 5 minutes), and the supernatant was collected. This procedure was repeated three times. The finally obtained supernatant was used as a xanthohumol saturated aqueous solution or an isoxanthohumol saturated aqueous solution. The saturated aqueous solution was 100-fold diluted with a 25% aqueous ethanol solution to obtain a sample for analysis. The sample was subjected to quantitative analysis using an LC-MS/MS system (TSQ Quantiva, Thermo Fisher Scientific Inc.) to evaluate the solubility in water. Table 5 shows the concentrations (ppm) of xanthohumol and isoxanthohumol in the supernatant. Note that ppm is ppm on w/v basis unless otherwise specified. Calibration curves of xanthohumol and isoxanthohumol were produced using the standard samples obtained in Preparation Example 1.

The LC-MS/MS measurement conditions for xanthohumol and isoxanthohumol are shown below.

<LC-MS/MS Analysis Conditions>

[HPLC Conditions]

The following solvents were used as mobile phases, and the following basic conditions and gradient conditions were applied.

(Basic Conditions)

Device: UltiMate 3000 (product name, Thermo Fisher Scientific Inc.)

Flow rate: 0.25 mL/min

Analysis time: 17.0 min/sample

Column: Atlantis T3, 2.1×150 (mm), particle size 3 μm

Column temperature: 40° C.

(Mobile Phase)

Phase A: 0.1% formic acid aqueous solution (Fisher Scientific)

Phase B: 0.1% formic acid-containing acetonitrile (Fisher Scientific)

(Gradient Conditions)

Table 4 shows gradient conditions. The percentage (%) of phase B is v/v %.

TABLE 4

| Time (min) | Ratio of phase B (%) |
|---|---|
| 0.0 | 15 |
| 1.5 | 15 |
| 6.0 | 100 |
| 14.0 | 100 |
| 14.1 | 15 |
| 17.0 | 15 |

[MS/MS Conditions]
Device: TSQ QUANTIVIA (product name, Thermo Fisher Scientific Inc.)
Measurement mode: MRM negative
Q1/Q3: 353.3>119.2
Injection quantity: 2 μL
(Experiment B: Study of Solubility of Isoxanthohumol in Various Solvents)

Distilled water, a hop extract, and 0.2% (w/v) or 1.0% (w/v) aqueous solution of β-cyclodextrin or γ-cyclodextrin (both Nacalai Tesque, Inc.) were prepared as solvents to study the solubility of isoxanthohumol under ice cooling conditions. As for the hop extract, hops (Saaz) that had been crushed into pellets were extracted with distilled water in an amount 10 times the weight of the pellets by shaking at room temperature for about 60 minutes, and the filtrate obtained by suction filtration was used for the test. The isoxanthohumol concentration in the hop extract was less than 0.5 ppm. A sample containing a solvent and isoxanthohumol having a weight corresponding to 0.2% (w/v) of the solvent was prepared for each of the above solvents, and the standard sample was allowed to dissolve in water as much as possible by stirring in a vortex mixer for 10 seconds or longer and shaking for about 60 minutes under ice cooling conditions. Centrifugation and quantitative analysis were performed as in Experiment A to evaluate the solubility of isoxanthohumol in each solvent. Table 6 shows the concentration (ppm) of isoxanthohumol in the supernatant.
(Results)

TABLE 5

|  | Solubility in water (ice cooling conditions) |
|---|---|
| Xanthohumol (XN) | Less than 0.5 ppm |
| Isoxanthohumol (IX) | 6.3 ppm |

TABLE 6

|  | Solvent | Solubility (ice cooling conditions) |
|---|---|---|
| Isoxanthohumol (IX) | Distilled water | 6.3 ppm |
|  | Hop extract | 13.7 ppm |
|  | 0.2% β-Cyclodextrin | 18.4 ppm |
|  | 1.0% β-Cyclodextrin | 52.0 ppm |
|  | 0.2% γ-Cyclodextrin | 33.6 ppm |
|  | 1.0% γ-Cyclodextrin | 115.5 ppm |

The above results clearly showed that isoxanthohumol has higher solubility in water than xanthohumol. In addition, it became clear that the solubility of isoxanthohumol can be improved by a hop extract, β-cyclodextrin, or γ-cyclodextrin.

INDUSTRIAL APPLICABILITY

The present invention is useful in the fields of foods, beverages, pharmaceutical products, and the like.

The invention claimed is:
1. A method of promoting lipid metabolism by promoting fat burning, comprising: administering orally a composition for promoting lipid metabolism comprising isoxanthohumol,
wherein the isoxanthohumol is administered to a human adult in an amount of 5 to 200 mg per 60 kg of body weight per day.
2. A method of suppressing fat accumulation by promoting fat burning, comprising: administering orally a composition for suppressing fat accumulation comprising isoxanthohumol,
wherein the isoxanthohumol is administered to a human adult in an amount of 5 to 200 mg per 60 kg of body weight per day.
3. A method of decreasing incidence of obesity or ameliorating obesity, comprising: administering orally a composition for anti-obesity comprising isoxanthohumol to promote lipid metabolism by promoting fat burning,
wherein the isoxanthohumol is administered to a human adult in an amount of 5 to 200 mg per 60 kg of body weight per day.

* * * * *